(12) United States Patent
Ranalletta

(10) Patent No.: US 7,316,669 B2
(45) Date of Patent: Jan. 8, 2008

(54) PROTECTIVE CAP FOR MEDICAL MALE LUER FITTINGS

(75) Inventor: Joseph V. Ranalletta, Englewood, CO (US)

(73) Assignee: Baxa Corporation, Englewood, CO (US)

( * ) Notice: Subject to any disclaimer, the term of this patent is extended or adjusted under 35 U.S.C. 154(b) by 115 days.

(21) Appl. No.: 10/226,599

(22) Filed: Aug. 22, 2002

(65) Prior Publication Data

US 2004/0039341 A1 Feb. 26, 2004

(51) Int. Cl.
*A61M 5/32* (2006.01)
(52) U.S. Cl. ...................... 604/199; 604/263
(58) Field of Classification Search ............... 604/192, 604/181, 187, 256, 533, 905, 198, 199, 111, 604/206, 241–243, 263
See application file for complete search history.

(56) References Cited

U.S. PATENT DOCUMENTS

| | | | |
|---|---|---|---|
| 5,535,785 A | 7/1996 | Werge et al. | 137/843 |
| 5,620,427 A * | 4/1997 | Werschmidt et al. | 604/535 |
| 5,702,374 A | 12/1997 | Johnson | 604/283 |
| 5,756,178 A * | 5/1998 | Obadia | 428/66.4 |
| 5,775,671 A | 7/1998 | Cote, Sr. | 251/149.8 |
| 5,788,215 A | 8/1998 | Ryan | 251/149.6 |
| 5,807,345 A | 9/1998 | Grabenkort | 604/199 |
| 5,851,201 A | 12/1998 | Ritger et al. | 604/240 |
| 5,855,230 A | 1/1999 | Guala et al. | 138/89 |
| 5,947,954 A | 9/1999 | Bonaldo | 604/533 |
| 5,954,313 A | 9/1999 | Ryan | 521/149.1 |
| 5,984,373 A | 11/1999 | Fitoussi et al. | 285/92 |
| 6,039,302 A | 3/2000 | Cote, Sr. et al. | 251/149.1 |
| 6,063,062 A | 5/2000 | Paradis | 604/249 |

(Continued)

OTHER PUBLICATIONS

Product Information Card by Baxter, Interlink Needle-Less IV Access System, 1 Page.
Information Page by Baxter, Interlink Needle-Less IV Access System, www.life-assist.com, 37 Pages.

*Primary Examiner*—Kevin C. Sirmons
*Assistant Examiner*—Laura C. Schell
(74) *Attorney, Agent, or Firm*—Marsh Fischmann & Breyfogle LLP

(57) ABSTRACT

An improved protective cap and method for capping medical male luer fittings is provided. The protective cap may include inner and intermediate annular members extending from an end wall and defining a slot therebetween. At least one and preferably a plurality of depressible members project from an outer surface of the inner annular member, wherein the depressible member(s) conforms to the internal threads of a male luer fitting upon interconnection. For such purposes, the depressible member(s) may comprise a resilient material, e.g. most preferably having a modulus of elasticity of between about 5000 psi and 20000 psi. Each depressible member may be of an arcuate configuration in cross-section to present a convex surface for depressible engagement by the collar of a male luer fitting when positioned in the annular slot. The protective cap may be readily employed in automated capping/uncapping procedures via direct linear advancement/retraction relative to a male luer fitting. The protective cap may also be readily rotated onto and off of a male luer fitting. The protective cap and associated methodologies are particularly apt for use in connection with syringes, including automated procedures for pre-filling disposable syringes with medical liquids.

62 Claims, 3 Drawing Sheets

U.S. PATENT DOCUMENTS

| | | | |
|---|---|---|---|
| 6,152,913 A * | 11/2000 | Feith et al. | 604/533 |
| 6,158,458 A | 12/2000 | Ryan | 137/515.5 |
| 6,171,287 B1 | 1/2001 | Lynn et al. | 604/256 |
| 6,217,560 B1 | 4/2001 | Ritger et al. | 604/243 |
| 6,267,154 B1 * | 7/2001 | Felicelli et al. | 141/18 |
| RE37,357 E | 9/2001 | Lynn | 604/533 |
| 6,332,633 B1 | 12/2001 | Fitoussi et al. | 285/332 |
| 6,394,983 B1 * | 5/2002 | Mayoral et al. | 604/192 |
| 6,491,667 B1 * | 12/2002 | Keane et al. | 604/192 |
| 7,214,214 B2 * | 5/2007 | Sudo et al. | 604/263 |

OTHER PUBLICATIONS

International Standard (ISO) 594/1 Conical fittings with a 6% (Luer) taper for syringes, needles and ceratin other medical equipmen—Part 1: General requirements, Ref. No. ISO 954/1-1986 (E).

International Standard (ISO) 594-2 Conical fittings with 6% (Luer) taper for syringes, needles and certain other medical equipment—Part 2: Lock fittings, Ref. No. ISO 594-2: 1998 (E).

\* cited by examiner

PROTECTIVE CAP FOR MEDICAL MALE LUER FITTINGS

FIELD OF THE INVENTION

The present invention relates to the capping and uncapping of medical male luer fittings utilized in medical liquid transfusion, infusion or injection applications. The protective cap is particularly apt for use in conjunction with disposable syringes and automated syringe capping systems.

BACKGROUND OF THE INVENTION

Male luer fittings are utilized in a wide variety of medical liquid transfusion, infusion and injection applications. By way of example, ISO standards 594-1 and 594-2 (i.e. as published by the International Organization for Standardization) set forth specifications for conventional male luer fittings.

In one primary use, male luer fittings are provided on disposable syringes for selectively receiving a hub from which a needle projects. The hub is sized to slidably and sealably receive a complimentary nozzle of the male luer fitting. Typically, to enhance the reliability of interconnection, the male luer fitting includes an annular collar that is disposed about the nozzle and internally threaded for rotatably engaging outer threads provided on the hub of the needle.

In another primary use, male luer fittings are utilized in combination with complimentary female luer fittings to provide for the ready interconnection/disconnection of medical liquid tubing lines and/or outlet ports of medical liquid sources. In such applications, the female luer fitting is sized to slidably and sealably receive a complementary nozzle of the male luer fitting. By way of example, the use of connectable male luer and female luer fittings facilitates the fluid interconnection/disconnection of patients to medical liquid sources during extended therapy and otherwise allows for the replacement of medical liquid sources and/or associated tubing line sets in the course of extended therapy. Typically, to enhance the reliability of interconnections, the male luer fitting includes an annular collar that surrounds the nozzle and is internally threaded to rotatably engage outer threads disposed on the female luer fitting.

In connection with the noted uses of male luer fittings, it is generally desirable to provide a protective cap on a male luer fitting prior to and/or in-between the intended interconnection(s). Such protective caps are generally utilized to maintain a desired degree of sterility at the nozzle of the male luer fitting. Further, when male luer fittings are used in connection with syringes filled with a medical liquid (e.g. pre-filled with a liquid medication or flush solution), protective caps may also function to prevent leakage of the contained medical liquid. Similarly, protective caps serve to preclude the passage of liquid through connectors employed in connection with medical liquid tubing lines and/or outlet ports of medical liquid sources.

Collared male luer fittings of the type noted above are often referred to as "luer lock fittings". When such luer lock fittings are utilized, protective caps employed therewith may be provided with interfacing annular members having external threads that are complimentary with the internally threaded collars of the male luer fittings. Such protective caps must necessarily be rotatably advanced/retracted relative to the male luer fittings in order to achieve interconnection/disconnection with the threaded collars. Further, in that regard, in automated systems for capping/uncapping collared male luer fittings (e.g. in conjunction with the automated assembly and/or filling of a disposable syringe), the utilization of protective caps having threaded annular members may increase equipment complexity since each protective cap and/or interfacing male luer fitting must be supportably disposed for both automated linear and rotational movement.

SUMMARY OF THE INVENTION

A broad objective of the present invention is to provide a protective cap that accommodates varying approaches for capping and uncapping a male luer fitting having a nozzle and surrounding collar.

A related objective of the present invention is to provide enhanced methods for the capping/uncapping of male luer fittings having a nozzle and surrounding collar, including automated syringe capping systems.

Yet a further objective of the present invention is to provide an improved protective cap for maintaining the sterility of and otherwise sealing the nozzle of a male luer fitting having a surrounding collar.

In addressing one or more of the noted objectives the present inventor has recognized the desirability of providing a protective cap that can be either pushed or rotated onto and pulled or rotated off of a collared male luer fitting. Further, the inventor has recognized the desirability of providing a protective cap that can be pushed on/pulled off of a male luer fitting a number of times in automated processes, yet maintain desired sterility and sealing capabilities.

The inventive protective cap includes an inner annular member extending from an end wall to define a cylindrical slot for receiving a nozzle of a male luer fitting, and at least one depressible member projecting from an outer surface of the inner annular member for depressibly engaging the collar threads of a male luer fitting. The depressible member(s) is disposed to crossover and interfere with the collar threads, wherein the collar threads depress the depressible member(s) when capped. For common male luer fitting applications, a predetermined interference of between about 0.005 and 0.020, and most preferably between about 0.010 and 0.015 may be defined between each depressible member and the collar threads.

The depressible member(s) preferably comprises a deformable material, wherein the depressible member(s) is deformable from an initial configuration to substantially conform to the shape of the collar threads of a male luer fitting when depressed thereby. Most preferably, the depressible member(s) comprises a resilient material capable of elastic deformation, wherein the depressible member(s) substantially "springs back", or returns, to its initial configuration after being depressed by the collar threads of a male luer fitting. In this regard, the depressible member(s) preferably display a modulus of elasticity of between about 965 and 34,000 psi, and most preferably between about 5,000 and 20,000 psi. As may be appreciated, this feature allows the protective cap to function in a self-threading manner whether rotated onto or pushed onto a male luer fitting and otherwise yield a repeatable, sealed interface therebetween (e.g. when repeatedly rotated or pushed onto and/or rotated or pulled off of a male luer fitting).

By way of example only, the depressible member(s) may comprise a resilient material selected from a group consisting of:
  thermoplastic elastomers;
  thermoplastic rubbers; and,
  thermoset rubbers.

Further, the entire protective cap may be integrally molded from one of the noted resilient materials.

The depressible member(s) may be provided so that it may be linearly pushed onto and/or pulled off of a collared male luer fitting with between about 3 lbs. and 10 lbs. of force, and most preferably with between about 3 lbs. and 6 lbs. of force. At the same time, the depressible member may be provided so that it may be either rotated on to and/or rotated off of a collared male luer fitting with less than about 1 in.-lbs. of torque, and most preferably between about 0.70 in-lbs. and 0.80 in.-lbs. of torque. As may be appreciated, the noted ranges readily accommodate automated push-on/pull-off and/or rotate-on/rotate-off processes (e.g. for automated uncapping, medical liquid filling, and recapping of disposable syringes), as well as manual rotate-on and/or rotate-off handling (e.g. at a patient site).

To facilitate sealing engagement with the collar threads of a male luer fitting, the depressible member(s) may continuously extend along a length of the inner annular member that is sufficient to crossover at least two adjacent, axially offset thread portions. In this regard, common male luer fitting collars comprise two commonly-configured threads that spiral from 180° offset locations. To facilitate sealing engagement with such male luer fittings, it is preferable for each depressible member(s) to continuously extend along a length sufficient to crossover each of the two threads presented by the collar of a male luer connector at least once.

In one application the depressible member(s) continuously extend along at least a majority of the distal-to-proximal length of the inner annular member. Additionally, the depressible member(s) may follow a substantially linear path that extends along the length of the inner annular member. Further, the linear path may extend substantially parallel to a common center axis of the protective cap and inner annular member.

To accommodate interconnection/disconnection with a male luer fitting it is also preferable that the depressible member(s) be of an arcuate or crescent configuration in cross-section, wherein an outward-facing, convex surface is presented for engagement with the collar threads of a male luer fitting. Further, each depressible member may be tapered at its distal end (i.e. the receiving end of the protective cap).

Preferably, a plurality of depressible members are provided; most preferably at least three. Such depressible members may be equally spaced about the inner annular member, may be of a common length and configuration, and may follow coincidental paths.

The protective cap may further include an intermediate annular member extending from the end wall and located about the inner annular member to define an annular slot therebetween for receiving the collar of a male luer fitting. For common applications, the annular receiving slot may have a maximum cross-width of between about 0.040 and 0.050 inches (e.g. as measured along a radius not passing through a depressible member), and each depressible member may have a cross-width or thickness of between about 0.010 and 0.020 inches.

In one embodiment the protective cap includes concentric inner and intermediate annular members that extend substantially the same distance from an end wall to define an annular slot therebetween. Further, four depressible members are equally spaced at 90° intervals about the outer surface of the inner annular member for depressibly engaging a collar of a male luer fitting when received in the annular receiving slot. The cylindrical slot defined by the inner annular member includes at least one tapered, or conical, portion for slidably and sealably receiving a tapered, or conical, nozzle of a male luer fitting.

In this embodiment, each of the depressible members are of a common configuration and extend rearwardly from the distal end of the inner annular member along substantially parallel, linear paths which are equally spaced about and run parallel to a center axis of the protective cap. Further, the four depressible members are of an arcuate or crescent configuration in cross-section, wherein four outward-facing convex surfaces are presented at 90° intervals within the annular slot for depressibly receiving a collar of a male luer fitting inserted thereinto. Each of the depressible members are tapered at their distal ends.

To further facilitate capping/uncapping, this protective cap embodiment also includes an outer annular member extending from the end wall and located about the intermediate member. The outer annular member may extend from the end wall to a distance lesser than that of the inner and intermediate annular members. The outer annular member may be readily held in an automated or manual procedure to yield enhanced force application for capping/uncapping procedures, particularly where manual rotation during uncapping is involved.

One or more features of the inventive protective cap may be incorporated into an inventive capped syringe product. In particular, a disposable syringe may include a barrel, a plunger slidably disposed within the barrel, and a male luer fitting located at a distal end of the barrel with a nozzle and a surrounding collar which define an annular slot therebetween. The capped syringe may further include a protective cap that is removably connected to the male luer fitting, wherein the protective cap includes an inner annular member extending from an end wall and at least one depressible member projecting from an outside surface of the annular member. The protective cap is disposed so that the annular member thereof is positioned within the annular slot of the male luer fitting and the depressible member(s) is at least partially depressed by the collar of the male luer fitting. Preferably, the depressible member(s) are sized and comprise a resilient material to yield conformability and sealing advantages as noted above. For some applications, the inventive product may further include an enclosure for sealably containing the syringe and protective cap.

The protective cap of the capped syringe may include a plurality of depressible members spaced about the outer surface of the inner annular member and configured to be of an arcuate or crescent shape in cross-section. Again, the depressible members may extend along corresponding, coincidental paths (e.g. substantially linear paths extending parallel to a center axis of the protective cap, syringe and male luer fitting). The protective cap may further include intermediate and outer annular members as described above.

In addition to the noted features, the barrel of the capped syringe may be filled with a medical liquid. In such applications, the medical liquid may be introduced prior to packaging and shipment. Alternatively, the medical liquid may be introduced at a patient care facility in conjunction with an automated syringe filling operation.

As may be appreciated, the present invention also yields enhanced methods for capping/uncapping a male luer fitting. In one aspect, a method is provided for capping a male luer fitting with a protective cap having an inner annular member extending from an end wall. The method includes an initial step of positioning the protective cap and male luer fitting in an aligned position. The method further includes the steps of advancing at least one of the protective cap and male luer fitting towards the other, and during at least a portion of the advancing step, depressing at least one depressible member that projects from an outer surface of the inner annular member of the protective cap via engagement by the internal threads of the collar of the male luer fitting. The inventive method may further include the step of retracting at least one of the protective cap and male luer fitting relative to the other, wherein the collar threads disengage the depressible member(s).

In relation to the depressing step, the depressible member(s) preferably elastically deforms to substantially conform to the shape of the collar threads of a male luer fitting as the depressible member(s) crosses over such threads, thereby yielding a secure and sealed engagement therebetween. Further, the depressible member(s) may be provided so as to substantially spring-back to an initial configuration after disengagement with the male luer fitting collar threads.

In conjunction with the inventive method, the advancement and retraction steps may be achieved by rotating at least one of the protective cap and male luer fitting relative to the other. During advancement/retraction, such rotation causes the collar threads of the male luer fitting to engage/disengage the depressible member(s) across spaced segments thereof in corresponding relation to the spacing between the collar threads. Alternatively, advancement and retraction may be achieved via simple linear advancement (e.g. pushing)/retraction (e.g. pulling) of one of the protective cap and male luer fitting relative to the other. Such linear advancement/retraction causes the internal collar threads of the male luer fitting to progressively engage the depressible member(s) along a portion of the length thereof in a distal-to-proximal/proximal-to-distal manner.

Of note, the inventive method may be advantageously employed in conjunction with automated processes. In such processes, the protective cap and male luer fitting may be positioned in corresponding holders, wherein at least one of the holders is disposed for driven linear and/or rotational advancement relative to the other. Most preferably, the holder for the protective cap may be linearly retracted and advanced again for automated uncapping and recapping. As may be appreciated, automation is significantly simplified by the capability to achieve reliable and repeatable capping/uncapping via linear advancement/retraction.

In one embodiment, the inventive method may be incorporated into an overall system for the handling, labeling, filling and capping syringes. One such system is disclosed in U.S. patent application Ser. No. 09/928,007, entitled "METHOD, SYSTEM, AND APPARATUS FOR HANDLING, LABELING, FILLING AND CAPPING SYRINGES", filed Aug. 10, 2001, hereby incorporated by reference in its entirety.

In conjunction with such system automated syringe filling may occur at a first location (e.g. at a production facility of a pharmacy of a medical care site). For example, a disposable syringe capped with a protective cap of the present invention may be positioned in a first holder. Then, a second holder may be advanced toward the first holder to engage and capture the protective cap. Upon linear retraction of the second holder, the protective cap is automatically removed, or pulled, from the disposable syringe. Then, the syringe may be automatically filled with a medical liquid (e.g. by flowing the medical liquid under pressure through the nozzle of a male luer fitting into the syringe). Thereafter, the second holder may be positioned to align the protective cap relative to the male luer fitting of the filled syringe. Finally, the second holder may be linearly advanced to position, or push, the protective cap on the filled syringe to a predetermined desired location with high and repeatable accuracy.

Subsequently, the filled syringe may be utilized by medical personnel at a second location (e.g. a patient site). For example, the protective cap may be manually rotated out of engagement with the male luer fitting of the syringe, whereupon at least a portion of the medical liquid may be administered to a patient. Thereafter, the protective cap may be reconnected to the syringe (e.g. rotatably advanced) for subsequent administrations or disposal, at the second location.

Additional aspects and advantages of the present invention will become apparent to those skilled in the art upon consideration of the further description provided hereinbelow.

DETAILED DESCRIPTION

Figure 1C:
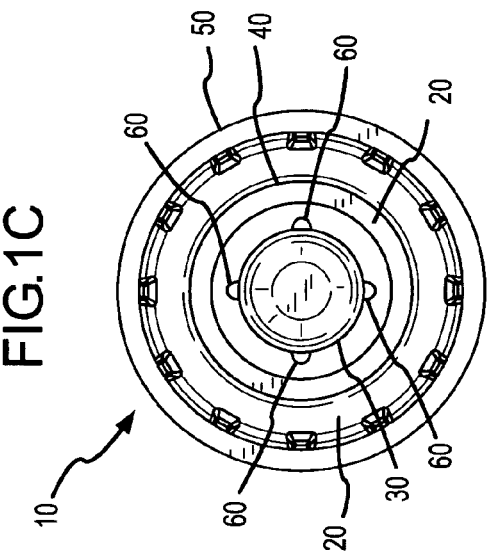
FIG. 1C illustrates a perspective view of the protective cap embodiment of FIGS. 1A and 1B.
Figure 1D:
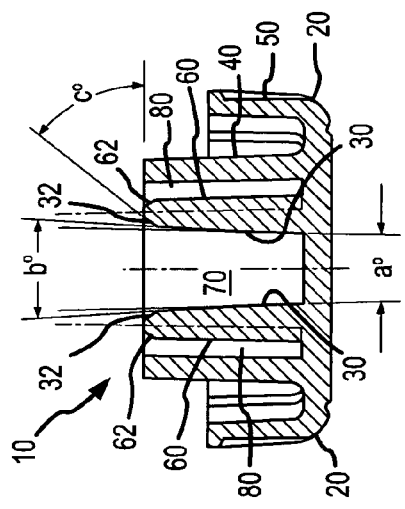
FIG. 1D illustrates a bottom plan view of the protective cap embodiment of FIGS. 1A-1C.
Figure 1A:
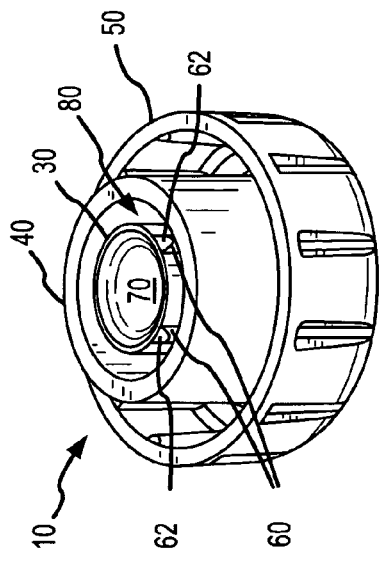
FIG. 1A illustrates a top plan view of one embodiment of a protective cap comprising the present invention.
Figure 1B:
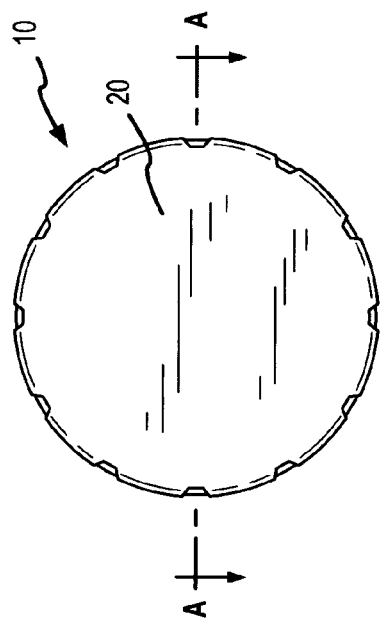
FIG. 1B illustrates a cross-sectional side view of the protective cap embodiment of FIG. 1A as taken along section line AA thereof.

FIGS. 1A-1D illustrate one embodiment of a protective cap 10 comprising the present invention. As shown, protective cap 10 comprises an end wall 20 having annular members 30, 40 and 50 extending therefrom. The annular members 30, 40 and 50 are concentrically positioned about a center axis of the protective cap 10. Inner and intermediate annular members 30 and 40, respectively, may extend substantially the same distance from the end wall 20 to their distal ends, while outer annular member 50 extends a lesser distance from the end wall 20. As best shown by FIG. 1B, inner annular member 30 defines a generally cylindrical center slot 70, and the inner and intermediate annular members 30 and 40, respectively, define an annular slot 80 therebetween. Slots 70 and 80 are sized and otherwise located for the receipt of the nozzle and collar of a male luer fitting. For common applications, the annular slot 80 may have a maximum cross-width of between about 0.040 and 0.050 inches (e.g. as measured along a radius not passing through a depressible member), and each depressible member may have a cross-width or thickness of between about 0.010 and 0.020 inches.

In the later regard, a number of depressible members 60 project from the outside surface of the inner annular member 30 and are disposed to crossover and interfere with the internal threads of the collar of a male luer fitting. For common male luer fitting applications, a predetermined interference of between about 0.005 and 0.020 inches, and most preferably between about 0.010 and 0.015 inches may be defined between each of the depressible members 60 and the collar threads.

In the illustrated protective cap 10 four depressible members 60 are positioned about the inner annular member 30 at 90° intervals and extend along the length of the inner annular member. Upon receipt of the collar of a male luer fitting (e.g. annular slot 80) depressible members 60 will be depressed by the internal threads of the collar to securely engage the male luer fitting.

To facilitate such functionality the depressible members 60 may be of an arcuate or crescent configuration in cross-section. Further, the depressible members 60 each include a leading tapered surface 62 at their distal end. In the embodiments of FIGS. 1A-1D, the depressible members 60 each extend along substantially coincidental linear paths. Such coincidental linear paths may be parallel in at least one dimension to a center axis of the protective cap 10.

Depressible members 60 may comprise a deformable and resilient material so that depressible members 60 can substantially conform to the shape of the internal collar threads of a male luer fitting when depressed thereby, and spring-back to substantially their initial configuration when disengaged from the collar threads. In this regard, the depressible members 60 preferably display a modulus of elasticity of between about 965 and 34,000 psi, and most preferably between about 5,000 and 20,000 psi. For such purposes, and by way of example only, the depressible members 60 may comprise a resilient material selected from a group consisting of:

thermoplastic elastomers;
thermoplastic rubbers; and,
thermoset rubbers.

More generally, the protective cap 10 may be integrally molded from a resilient material, e.g. those identified above.

As noted, slot 70 of protective cap 10 is adapted to receive the nozzle of a male luer fitting inserted thereinto. In this regard, the nozzle of a conventional male luer fitting is of a conical, or tapered, configuration. To accommodate such nozzles, the slot 70 may comprise two or more sidewall portions that angle away from the center axis of the protective cap 10 to differing degrees. By way of example, in the protective cap 10 shown in FIG. 1B a first portion of the internal sidewalls of inner annular member 30 may define a contained angle of a, and a second portion of the inner sidewalls of the inner annular member 30 may define a contained angle of b. Additionally, to facilitate the receipt of a conical nozzle 110 of a male luer fitting the inner annular member 30 may be provided with a tapered surface 32 at its distal end. Such tapered surface forms an angle of c relative to a tangent plane at the distal end of the inner annular member 30. Preferably, $3°<a<4°$, $7°<b<10°$ and $45°<c<60°$.

Figure 2A:
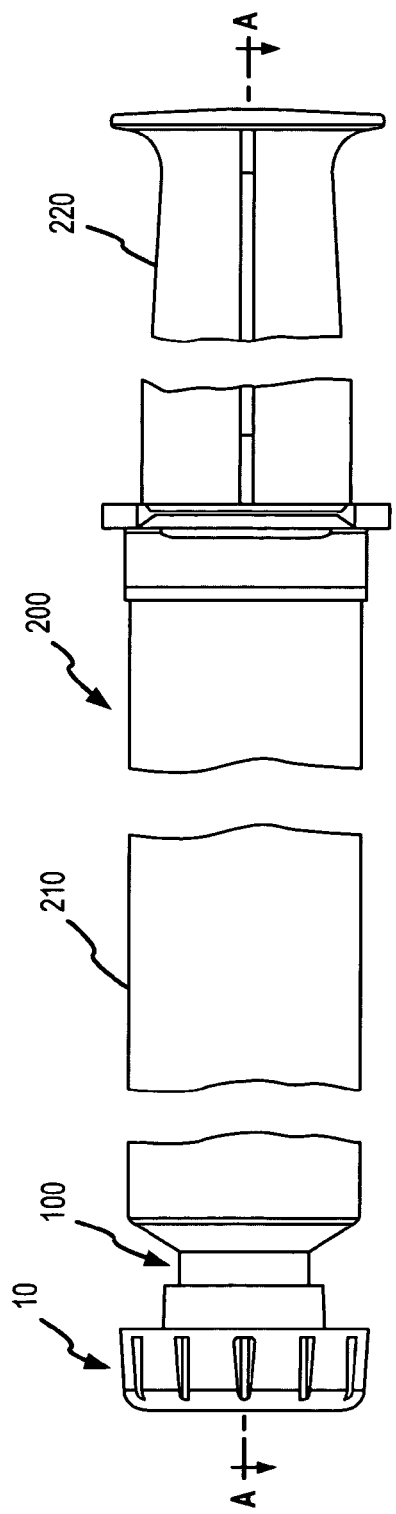
FIG. 2A illustrates a side view of the protective cap embodiment of FIGS. 1A-1D as interconnected to a male luer fitting of an exemplary syringe.
Figure 2B:
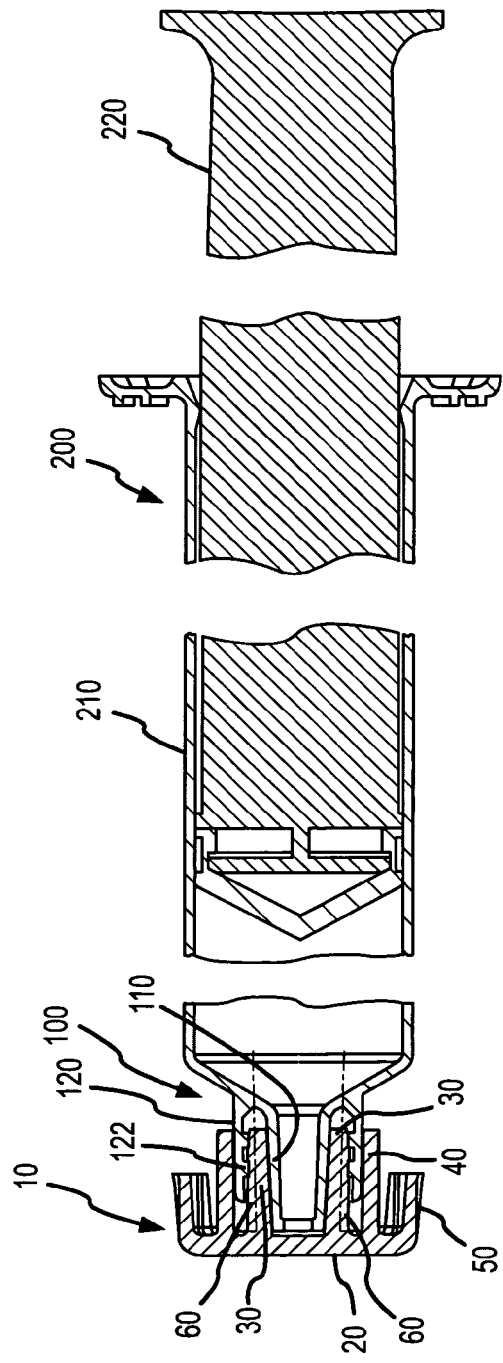
FIG. 2B is a cross-sectional side view of the capped syringe of FIG. 2A, as taken along section line AA thereof.

Reference is now made to FIGS. 2A and 2B which illustrate protective cap 10 positioned on a male luer fitting 100 disposed at the distal end of an exemplary syringe 200. More particularly, syringe 200 includes a barrel portion 210 and plunger portion 220. The male luer fitting 100 includes conical nozzle 110 and an annular collar member 120 concentrically disposed thereabout. The inner sidewall of the annular collar member 120 includes spiraling internal threads 122 projecting therefrom (e.g. two continuous threads starting at 180° offset locations).

As illustrated in FIG. 2B, when protective cap 10 is positioned on male luer fitting 100 the internal threads 122 of the annular collar member 120 depress the depressible members 60 provided on the outside surface of the inner annular member 30. More particularly, depressible members 60 are deformed to a substantially conformal shape relative to the internal threads 122 of the annular collar 120. As a result, protective cap 10 is securely interconnected to the male luer fitting 100 and substantially precludes fluid passage therebetween.

The retentive engagement illustrated by FIG. 2B can be advantageously achieved in a number of ways. Such options will be described in relation to FIGS. 3A, 3B and 3C which show a male luer fitting 100 and a protective cap 10 in various relative positions.

Figure 3A:
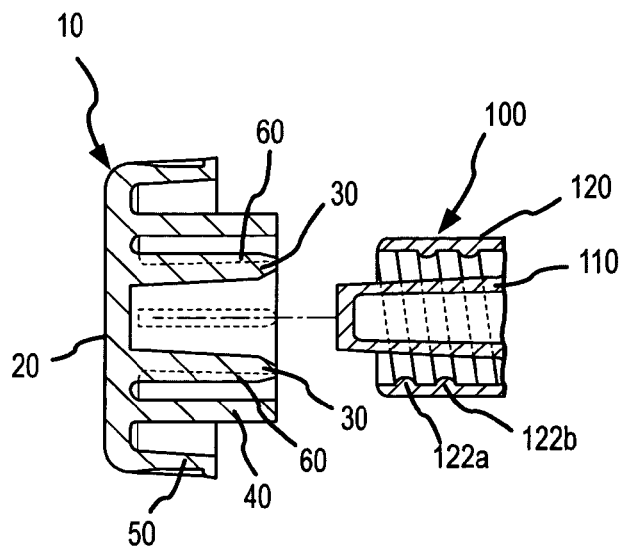
FIGS. 3A, 3B and 3C are cross-sectional side views of the protective cap embodiment of FIGS. 1A-1D being interconnected to an exemplary male luer fitting.
Figure 3B:
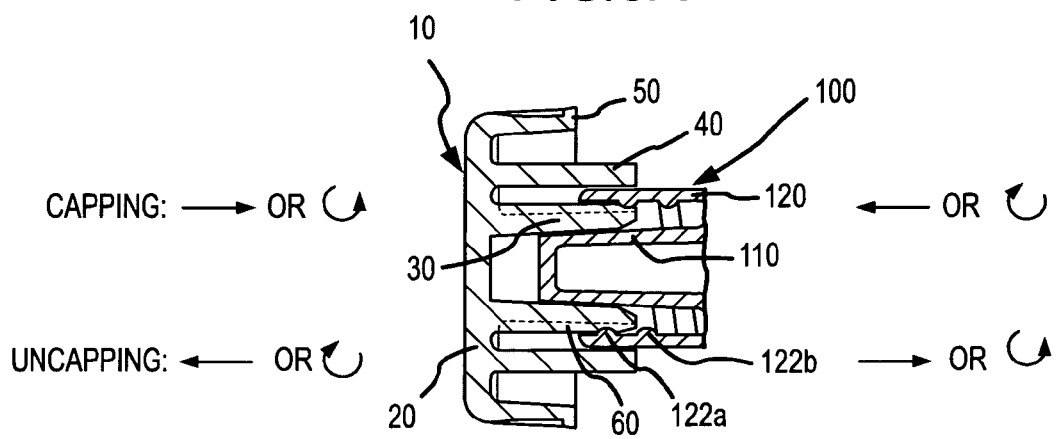
Figure 3C:
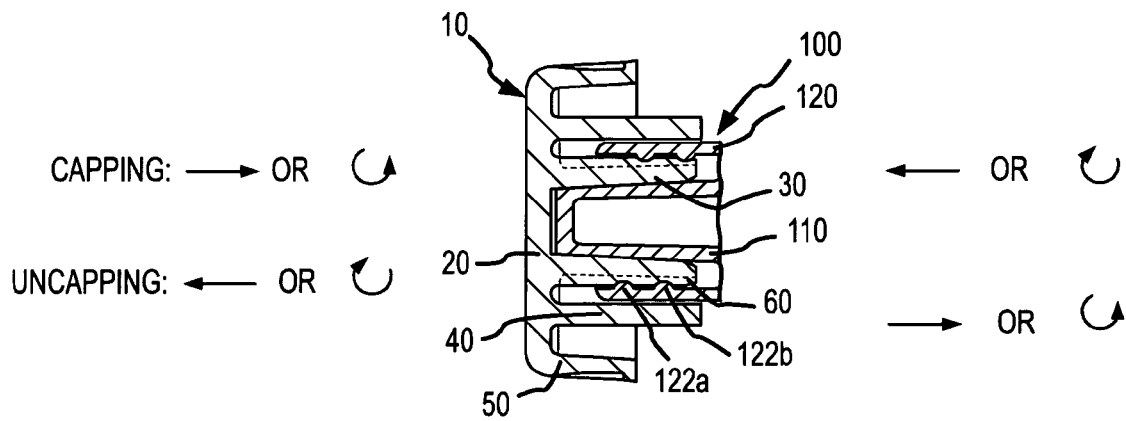

In a first capping approach, the protective cap 10 and male luer fitting 100 may be initially aligned relative to one another as illustrated in FIG. 3A. Male luer fitting 100 comprises two coincidental threads 122a, 122b, which are commonly configured and which spiral from 180° offset locations. Upon engagement of the male luer fitting 100 and protective cap 10 one or both may be rotatably advanced relative to the other, wherein spaced segments of the internal threads 122a, 122b depress the depressible members 60 as shown in FIG. 3B. More particularly, upon further rotative advancement spaced segments of both threads 122a, 122b may depress each depressible member at least once, as shown in FIG. 3C. To disengage the protective cap 10 and male luer fitting, one or both may be rotatably retracted as shown in FIGS. 3B and 3C. Preferably, protective cap 10 may be provided so that rotative capping and rotative uncapping procedures may be completed with the application of less than about 1 in.-lbs. of torque, and most preferably between about 0.70 in.-lbs. and 0.80 in.-lbs. of torque. Such torque ranges readily accommodate manual procedures.

In another approach, the protective cap 10 and syringe 200 may be initially aligned relative to one another as illustrated in FIG. 3A. Male luer fitting 100 comprises two coincidental threads 122a, 122b, which are commonly configured and which spiral from 180° offset locations. Upon engagement of the male luer fitting 100 and protective cap 10 one or both may be linearly advanced relative to the other, wherein internal threads 122 progressively depress the depressible members 60 in a distal-to-proximal manner along a portion of the length of the depressible members 60. Linear advancement preferably continues a predetermined distance until spaced segments of both threads 122a, 122b depress each depressible member at least once, as shown in FIG. 3C. To disengage the protective cap 10 and syringe 200, one or both may be linearly retracted. Preferably, protective cap 10 may be provided so that linear capping and linear uncapping procedures may be completed with the application of between about 3 lbs. and 10 lbs. of force, and most preferably, between about 3 lbs. and 6 lbs. of force. Such force ranges can be easily accommodated by automated procedures.

In the later regard, protective cap 10 may be advantageously utilized in conjunction with automated male luer fitting capping/uncapping, and in particular syringe filling procedures. In such procedures, one or a series of syringes such as exemplary syringe 200 may be filled with a medical liquid prior to or after positioning within corresponding syringe holders. Correspondingly, one or a plurality of protective caps 10 may be positioned in cap holders, wherein the syringe holders and cap holders are disposed for driven movement relative to each other in one to one relation. As may be appreciated, the automated, driven motion may be provided as described above in relation to FIGS. 3A, 3B and 3C so that the filled syringes 200 are automatically capped by protective caps 10 for subsequent use.

By way of particular example, protective cap 10 may be employed in conjunction with an automated syringe handling, labeling, filling and capping system, as disclosed in U.S. patent application Ser. No. 09/928,007, entitled "METHOD, SYSTEM, AND APPARATUS FOR HANDLING, LABELING, FILLING AND CAPPING SYRINGES", filed Aug. 10, 2001, hereby incorporated by reference in its entirety. In such system, a plurality of syringes such as exemplary syringe 200 may be interconnected in a predetermined orientation by a belt. The belt may be of pliable construction and may define a predetermined spacing in between adjacent ones of the syringes 200. In turn, such predetermined spacing may correspond with a distance between syringe holders provided by a handling apparatus. For example, the handling apparatus may comprise a rotatable member having a number of notches located thereabout for holding the interconnected syringes 200. Optionally, the handling apparatus may further provide for placement of contents-related information on belt segments between adjacent syringe bodies and for separating the belt segments. Further, the syringe handling apparatus may provide for automated filling of the syringe bodies. More particularly, protective caps 10 may be automatically taken off and positioned back on each of the syringes 200 via relative linear retraction and advancement of syringe and protective cap holders, with automated filling of the syringes 200 occurring between the uncapping and recapping steps.

As may be appreciated the noted automated steps may be completed at a first location (e.g. a production facility or pharmacy of a medical care facility). Subsequently, given filled syringe 200 may be utilized at a second location (e.g. patient care sire), wherein the protective cap 10 may be manually removed (e.g. via rotation) and replaced as desired.

The embodiments described above are for exemplary purposes only and is not intended to limit the scope of the present invention. Various adaptations, modifications and extensions of the embodiment will be apparent to those skilled in the art and are intended to be within the scope of the invention as defined by the claims which follow.

What is claimed:

1. A protective cap for use on a male luer fitting having a tapered, conical nozzle, comprising:
    a first annular member extending from an end wall, wherein said first annular member includes an internal sidewall portion that defines a cylindrical slot having at least one tapered, conical section sized for slidably and sealably receiving therein said tapered, conical nozzle of said male luer fitting;
    at least one depressible member, projecting outward from an outer surface of said first annular member, for depressibly engaging internal collar threads of said male luer fitting when interconnected thereto; and,
    an intermediate annular member extending from said end wall and located about said first annular member to define an annular slot therebetween for receiving a collar of said male luer fitting.

2. A protective cap as recited in claim 1, further comprising:
    a plurality of depressible members, projecting from and spaced about said outer surface of said first annular member, for depressibly engaging internal collar threads of said male luer fitting interconnected thereto.

3. A protective cap as recited in claim 2, wherein said plurality of depressible members are substantially equally spaced about said outer surface of said first annular member.

4. A protective cap as recited in claim 2, wherein said plurality of depressible members extend along corresponding, coincidental paths.

5. A protective cap as recited in claim 2, wherein said plurality of depressible members extend along coincidental linear paths.

6. A protective cap as recited in claim 2, wherein said protective cap is linearly advanceable and retractable relative to internal threads of said male luer fitting with between about 3 lbs. and 10 lbs. of applied force and wherein said protective cap is rotatably advanceable and retractable relative to internal threads of said male luer fitting with less than about 1 in.-lbs. of applied torque.

7. A protective cap as recited in claim 1, wherein said at least one depressible member continuously extends along at least a majority of the length of the first annular member.

8. A protective cap as recited in claim 1, wherein said at least one depressible member is of an arcuate configuration in cross-section.

9. A protective cap as recited in claim 1, wherein said at least one depressible member is tapered at its distal end.

10. A protective cap as recited in claim 1 wherein said at least one depressible member comprises a deformable material to substantially conform to the shape of internal collar threads of said male luer fitting when interconnected thereto.

11. A protective cap as recited in claim 1, wherein said at least one depressible member comprises a resilient material having a modulus of elasticity of between 5,000 and 20,000 psi.

12. A protective cap as recited in claim 1 wherein said at least one depressible member comprises a resilient material selected from a group consisting of:
    thermoplastic elastomers;
    thermoplastic rubbers; and,
    thermoset rubbers.

13. A protective cap as recited in claim 1, wherein said protective cap is integrally defined by a molded resilient material selected from a group consisting of:
    thermoplastic elastomers;
    thermoplastic rubbers; and,
    thermoset rubbers.

14. A protective cap as recited in claim 1, wherein said at least one depressible member has a thickness of between about 0.01 in. and 0.02 in.

15. A protective cap as recited in claim 1, wherein said first annular member and intermediate annular member extend substantially the same distance from said end wall.

16. A protective cap as recited in claim 1, wherein said annular slot has a maximum cross width of between about 0.040 in, and 0.050 in.

17. A protective cap as recited in claim 1, wherein said protective cap further includes:
    an outer annular member located about said intermediate annular member and extending from said end wall to a distance lesser than that of said first annular member and said intermediate annular member.

18. A protective cap for use on a male luer fitting having a tapered, conical nozzle, comprising:
    a first annular member extending from an end wall, wherein said first annular member includes an internal sidewall portion that defines a cylindrical slot having at least one tapered, conical section sized for slidably and sealably receiving therein said tapered, conical nozzle of said male luer fitting , wherein said cylindrical slot has at least a first conical portion defining a contained angle of at least 3°;

at least one depressible member, projecting outward from an outer surface of said first annular member, for depressibly engaging internal collar threads of said male luer fitting when interconnected thereto; and, an intermediate annular member extending from said end wall and located about said first annular member to define an annular slot therebetween for receiving a collar of said male luer fitting.

19. A protective cap as recited in claim 18, wherein said cylindrical slot has a second conical portion and wherein said second conical portion adjoins said first conical portion and defines a contained angle of between about 7° to 10°.

20. A protective cap for use on a male luer fitting having a tapered, conical nozzle, comprising:

a first annular member extending from an end wall, wherein said first annular member defines a cylindrical slot having at least one tapered, conical section sized for slidably and sealably receiving said tapered, conical nozzle of said male luer fitting;

at least one depressible member, projecting outward from an outer surface of said first annular member, for depressibly engaging internal collar threads of said male luer fitting when interconnected thereto, wherein said at least one depressible member is disposed to interfere with internal collar threads of a male luer fitting when interconnected thereto, with said interference being between about 0.005 in. and 0.020 in.; and, an intermediate annular member extending from said end wall and located about said first annular member to define an annular slot therebetween for receiving a collar of said male luer fitting.

21. A protective cap for use on a male luer fitting having a tapered, conical nozzle, comprising:

a first annular member extending from an end wall, wherein said first annular member defines a cylindrical slot having at least one tapered, conical section sized for slidably and sealably receiving said tapered, conical nozzle of said male luer fitting; and, a plurality of depressible members, projecting outward from an outer surface of said first annular member, for depressibly engaging internal collar threads of said male luer fitting when interconnected thereto, wherein said protective cap is linearly advanceable and retractable relative to internal threads of said male luer fitting with between about 3 lbs. and 10 lbs. of applied force, and wherein said protective cap is rotatably advanceable and retractable relative to internal threads of said male luer fitting with less than about 1 in.-lbs. of applied torque.

22. A protective cap as recited in claim 21, wherein said plurality of depressible members are substantially equally spaced about said outer surface of said first annular member.

23. A protective cap as recited in claim 21, wherein said plurality of depressible members extend along corresponding, coincidental paths.

24. A protective cap as recited in claim 21, wherein said plurality of depressible members extend along coincidental linear paths.

25. A protective cap as recited in claim 21, wherein said plurality of depressible members continuously extend along at least the majority of the length of said first annular member.

26. A protective cap as recited in claim 21, wherein each of said plurality of depressible members is tapered at its distal end.

27. A protective cap as recited in claim 21, wherein each of said plurality of depressible members comprises a deformable material to substantially conform to the shape of internal collar threads of said male luer fitting when interconnected thereto.

28. A protective cap as recited in claim 21, each of said plurality of depressible members comprises a resilient material having a modulus of elasticity of between 965 and 34,000 psi.

29. A protective cap as recited in claim 21, wherein each of said plurality of depressible members comprises a resilient material selected from a group consisting of:
thermoplastic elastomers;
thermoplastic rubbers; and,
thermoset rubbers.

30. A protective cap as recited in claim 21, wherein said protective cap is integrally defined by a molded resilient material selected from a group consisting of:
thermoplastic elastomers;
thermoplastic rubbers; and,
thermoset rubbers.

31. A protective cap as recited in claim 21, each of said plurality of depressible members has a thickness of between about 0.01 in, and 0.02 in.

32. A protective cap as recited in claim 21, further comprising:

an intermediate annular member extending from said end wall and located about said first annular member to define an annular slot therebetween for receiving a collar of said male luer fitting.

33. A protective cap as recited in claim 32, wherein said annular slot has a maximum cross width of between about 0.040 in. and 0.050 in.

34. A protective cap as recited in claim 32, wherein said first annular member and intermediate annular member extend substantially the same distance from said end wall, and wherein said protective cap further includes:

an outer annular member located about said intermediate annular member and extending from said end wall to a distance lesser than that of said first annular member and said intermediate annular member.

35. A protective cap as recited in claim 32, wherein each of said plurality of depressible members is disposed to interfere with internal collar threads of a male luer fitting when interconnected thereto, with said interference being between about 0.005 in. and 0.020 in.

36. A protective cap as recited in claim 21, wherein said cylindrical slot has at least a first conical portion defining a contained angle of at least 3°.

37. A protective cap as recited in claim 36, wherein said cylindrical slot has a second conical portion and wherein said second conical portion adjoins said first conical portion and defines a contained angle of between about 7° to 10°.

38. A protective cap for use on a male luer fitting having a tapered, conical nozzle, comprising:

a first annular member extending from an end wall, wherein said first annular member includes an internal sidewall portion that defines a cylindrical slot having at least one tapered, conical section sized for slidably and sealably receiving therein said tapered, conical nozzle of said male luer fitting; and, at least one depressible member, projecting outward from an outer surface of said first annular member, for depressibly engaging internal collar threads of said male luer fitting when interconnected thereto.

39. A protective cap as recited in claim 38, further comprising:

a plurality of depressible members, projecting from and spaced about said outer surface of said first annular member, for depressingly engaging internal collar threads of said male luer fitting interconnected thereto.

40. A protective cap as recited in claim 39, wherein said plurality of depressible members extend along corresponding, coincidental paths.

41. A protective cap as recited in claim 39, wherein said protective cap is linearly advanceable and retractable relative to internal threads of said male luer fitting with between about 3 lbs. and 10 lbs. of applied force, and wherein said protective cap is rotatably advanceable and retractable relative to internal threads of said male luer fitting with less than about 1 in.-lbs. of applied torque.

42. A protective cap as recited in claim 38, wherein said at least one depressible member comprises a deformable material to substantially conform to the shape of internal collar threads of said male luer fitting when interconnected thereto.

43. A protective cap as recited in claim 38, wherein said at least one depressible member comprises a resilient material having a modulus of elasticity of between 965 and 34,000 psi.

44. A protective cap as recited in claim 38, wherein said protective cap is integrally defined by a molded resilient material selected from a group consisting of:
 thermoplastic elastomers;
 thermoplastic rubbers; and,
 thermoset rubbers.

45. A protective cap as recited in claim 38, further comprising:
 an intermediate annular member extending from said end wall and located about said first annular member to define an annular slot therebetween for receiving a collar of said male luer fitting.

46. A protective cap as recited in claim 45, wherein said first annular member and intermediate annular member extend substantially the same distance from said end wall.

47. A protective cap as recited in claim 46, further comprising:
 an outer member located about said intermediate annular member and extending from said end wall to a distance that is less than distances to which said first annular member and said intermediate annular member extend from such end wall.

48. A protective cap as recited in claim 38, wherein said cylindrical slot has at least a first conical portion defining a contained angle of at least 3°.

49. A protective cap as recited in claim 48, wherein said cylindrical slot has a second conical portion and wherein said second conical portion adjoins said first conical portion and defines a contained angle of between about 7° to 10°.

50. A protective cap for use on a male luer fitting having a tapered, conical nozzle, comprising:
 a first annular member extending from an end wall, wherein said first annular member defines a cylindrical slot having at least one tapered, conical section sized for slidably and sealably receiving said tapered, conical nozzle of said male luer fitting; and,
 at least one depressible member, projecting outward from an outer surface of said first annular member, for depressibly engaging internal collar threads of said male luer fitting when interconnected thereto;
 an intermediate annular member extending from said end wall and located about said first annular member to define an annular slot therebetween for receiving a collar of said male luer fitting; and,
 an outer member located about said intermediate annular member and extending from said end wall to a distance that is less than distances to which said first annular member and said intermediate annular member extend from said end wall.

51. A protective cap as recited in claim 50, further comprising:
 a plurality of depressible members, projecting from and spaced about said outer surface of said first annular member, for depressibly engaging internal collar threads of said male luer fitting interconnected thereto.

52. A protective cap as recited in claim 51, wherein said plurality of depressible members extend along corresponding, coincidental paths.

53. A protective cap as recited in claim 51, wherein said protective cap is linearly advanceable and retractable relative to internal threads of said male luer fitting with between about 3 lbs. and 10 lbs. of applied force, and wherein said protective cap is rotatably advanceable and retractable relative to internal threads of said male luer fitting with less than about 1 in-lbs. of applied torque.

54. A protective cap as recited in claim 50, wherein said at least one depressible member comprises a deformable material to substantially conform to the shape of internal collar threads of said male luer fitting when interconnected thereto.

55. A protective cap as recited in claim 50, wherein said at least one depressible member comprises a resilient material having a modulus of elasticity of between 965 and 34,000 psi.

56. A protective cap as recited in claim 50, wherein said protective cap is integrally defined by a molded resilient material selected from a group consisting of:
 thermoplastic elastomers;
 thermoplastic rubbers; and,
 thermoset rubbers.

57. A protective cap as recited in claim 50, wherein said annular slot has a maximum cross width of between about 0.040 in. and 0.050 in.

58. A protective cap as recited in claim 50, wherein said first annular member and intermediate annular member extend substantially the same distance from said end wall.

59. A protective cap for use on a male luer fitting having a tapered, conical nozzle, comprising:
 a first annular member extending from an end wall, wherein said first annular member includes an internal sidewall portion that defines a cylindrical slot having at least one tapered, conical section sized for slidably and sealably receiving therein said tapered, conical nozzle of said male luer fitting;
 at least one depressible member, projecting outward from an outer surface of said first annular member, for depressibly engaging internal collar threads of said male luer fitting when interconnected thereto, wherein said at least one depressible member comprises a resilient material having a modulus of elasticity of between 5,000 and 20,000 psi; and,
 an intermediate annular member extending from said end wall and located about said first annular member to define an annular slot therebetween for receiving a collar of said male luer fitting.

60. A protective cap for use on a male luer fitting having a tapered, conical nozzle, comprising:
 a first annular member extending from an end wall, wherein said first annular member defines a cylindrical slot having at least one tapered, conical section sized for slidably and sealably receiving said tapered, conical nozzle of said male luer fitting;

at least one depressible member, projecting outward from an outer surface of said first annular member, for depressibly engaging internal collar threads of said male luer fitting when interconnected thereto, wherein said at least one depressible member has a thickness of between about 0.01 in. and 0.02 in.; and, an intermediate annular member extending from said end wall and located about said first annular member to define an annular slot therebetween for receiving a collar of said male luer fitting.

61. A protective cap for use on a male luer fitting having a tapered, conical nozzle, comprising:

a first annular member extending from an end wall, wherein said first annular member defines a cylindrical slot having at least one tapered, conical section sized for slidably and sealably receiving said tapered, conical nozzle of said male luer fitting;

at least one depressible member, projecting outward from an outer surface of said first annular member, for depressibly engaging internal collar threads of said male luer fitting when interconnected thereto; and, an intermediate annular member extending from said end wall and located about said first annular member to define an annular slot therebetween for receiving a collar of said male luer fitting, wherein said annular slot has a maximum cross width of between about 0.040 in. and 0.050 in.

62. A protective cap for use on a male luer fitting having a tapered, conical nozzle, comprising:

a first annular member extending from an end wall, wherein said first annular member includes an internal sidewall portion that defines a cylindrical slot having at least one tapered, conical section sized for slidably and sealably receiving therein said tapered, conical nozzle of said male luer fitting; and, at least one depressible member, projecting outward from an outer surface of said first annular member, for depressibly engaging internal collar threads of said male luer fitting when interconnected thereto, wherein said at least one depressible member comprises a resilient material having a modulus of elasticity of between 965 and 34,000 psi.

* * * * *